United States Patent [19]

Liegeois

[11] Patent Number: 5,536,544
[45] Date of Patent: Jul. 16, 1996

[54] FLEXIBLE OR RIGID COMBINATIONS OF MATERIALS IN COMPOSITE FORM WHICH ARE FORMABLE AND ADHESIVE AT TEMPERATURES BELOW 90° C.

[76] Inventor: Jean M. Liegeois, 411 Moulin de Wadeleux, B-4654, Herve, Belgium

[21] Appl. No.: 397,085

[22] PCT Filed: Sep. 7, 1993

[86] PCT No.: PCT/BE93/00057

§ 371 Date: Mar. 7, 1995

§ 102(e) Date: Mar. 7, 1995

[87] PCT Pub. No.: WO94/05339

PCT Pub. Date: Mar. 17, 1994

[30] Foreign Application Priority Data

Sep. 7, 1992 [BE] Belgium ................................. 9200787

[51] Int. Cl.⁶ ................................................. B29D 22/00
[52] U.S. Cl. ...................... 428/36.1; 427/243; 427/381; 428/35.7; 428/35.9; 428/36.8; 428/109; 428/131; 428/137; 428/247; 428/253; 602/41; 602/1; 604/304
[58] Field of Search ............................ 428/109, 131, 428/137, 247, 253, 35.7, 35.9, 36.1, 36.8; 427/243, 381; 602/1, 41; 604/304

[56] References Cited

U.S. PATENT DOCUMENTS

| | | | |
|---|---|---|---|
| 4,105,025 | 8/1978 | Wang et al. | 128/90 |
| 4,143,655 | 3/1979 | Custer et al. | 128/90 |
| 4,273,115 | 6/1981 | Holland et al. | 128/90 |
| 4,316,457 | 2/1982 | Liegeois | 128/90 |
| 4,326,509 | 4/1982 | Usuhura | 128/90 |
| 4,454,873 | 6/1984 | Laufenberg et al. | 128/90 |

FOREIGN PATENT DOCUMENTS

| | | |
|---|---|---|
| 0413339 | 2/1991 | European Pat. Off. |
| 2376170 | 7/1978 | France . |
| 3605192 | 11/1986 | Germany . |
| 62-038 | 2/1987 | Japan . |

*Primary Examiner*—James J. Bell
*Attorney, Agent, or Firm*—John F. A. Earley; John F. A. Earley, III

[57] ABSTRACT

Combinations of materials in composite form, which are thermoadhesive to themselves by treatment at temperatures not exceeding 90° C. and which can be shaped in the form of a laminate at said temperature, are characterized in that they comprise an open mesh textile substrate first impregnated or coated with a first rubber-like elastoviscous constituent having a softening point not exceeding 90° C. and further coated with a second, semi crystalline constituent essentially of polyester type having a fusion temperature from 35° to 80° C. These combinations have controlled adhesiveness and adequate fluidity for easy application by hand, particularly in do-it-yourself applications, orthopedics, sport and physiotherapy.

28 Claims, No Drawings

FLEXIBLE OR RIGID COMBINATIONS OF MATERIALS IN COMPOSITE FORM WHICH ARE FORMABLE AND ADHESIVE AT TEMPERATURES BELOW 90° C.

This invention relates to new composite combinations, in sheets, plaques, strips or laminates that are thermomalleable and thermoadhesive to themselves, flexible or rigid, with rather short setting time, and to preparation processes of those composite combinations.

Besides usual applications of plastics, there are various potential domains of applications wherein it is required to realize at every occasion a unique part or assembly with a material that one desires to mold, form or shape preferably manually and with a simple pre treatment such as heating at an easily accessible temperature.

Through the preparation treatment for their use, those materials must therefore have an adequate formability as well as an adhesive potential to themselves. The herein envisioned preparation treatment is limited to a temperature conditioning which will be detailed later, excluding the use of any solvent or external adhesive.

The application being in view can bear on an object or a creation as rigid as possible or one can seek in the application for some degree of flexibility to be selected according to the situation.

Such applications are often sought by individuals having not necessarily a great dexterity, who are willing to practice themselves without sophisticated technical means, realizing the molding, the shaping or the assembly principally by hand with the eventual help of a few simple tools such as scissors, clamps and holders. Obviously, the applications in view here can also be practiced by professionals operating in an industrial environment but that is not required.

As a result those forming and laminating applications must be realized from a pre-treatment temperature that remains accessible without risk of burns or other disadvantage that may cause clumsiness or an accident.

The used material must lose its adhesive property once it returns to ambient temperature and also keep the shape it was given and it must be capable to withstand mechanical stresses to which it may be exposed and not lose its shape up to a temperature as high as possible governed by the application.

A pre-treatment temperature range from 40° C. to 80° C. seems to be suitable, In any case under 100° C. so that such preparation can be done easily and relatively quickly by using hot water for example. It makes sense that alternative heating sources can be used also such as the thermal oven, the heat gun or the microwave oven.

Considering the applications in view, it is also recommended that those materials are inert and do not release substances that are toxic, irritating or with another noxious character so that the user can apply them without any particular safety mean.

Those products must also be stable for a long period of time without being subject neither to chemical ageing nor preferably to any physical ageing.

Therefore it should not be necessary to have to use sophisticated packaging such as hermetically sealed pouches subjected to tearing and that compromise the use of the material once the pouch has been opened as it can be the case in the application of the european patent 0 413 399 A1.

There are already a few domains of applications of the type of product addressed by this invention where one uses composites that are thermoformable and thermoadhesive as from a temperature of treatment from about 70° C. to 80° C. and that are essentially restricted to uses where a high rigidity is looked for. This concerns principally the physiotherapy where splints, orthoses and other means of rigid support are already made like that, the orthopedics interested with said thermoplastic bandages for cylindrical casting or with external prostheses made of same material, but also the field of decoration where stage scenery, masks and various objects essentially in three dimensions are made like that by laminating 2 or more layers.

In order to obtain the effect of formability and adhesiveness in the desired temperature range, one has principaly linear polymers of cyclic esters characterized by "COO" moieties apart one to another with methylene radicals comprising 2 to 7 carbon atoms of which the principal available representative is the polymer of 2-oxepanone better known under the popular name of polycaprolactone (PCL). The U.S. Pat. No. 3,692,023 suggests the use of that polymer to obtain immobilization devices from a substrate coated with the polymer and the french patent 2,376,170 leads to the same results by a just better performing process. In other respects, the U.S. Pat. No. 4,273,115 recommends a particular Raschel knitted fabric partially impregnated with that PCL polymer having a molecular weight of about 40 000 as material for cylindrical casting. Finally, in the U.S. Pat. No. 4,316,457, one has proposed the preparation of a linear thermoplastic polyurethane having a molecular weight from 40,000 to 45,000, synthesized in two steps where a prepolymer based on two moles of diisocyanate and one mole of polyester diol is added with one mole of polyester diol prior to impregnation of a Raschel knitted web to build chain extension while completing the polymerization on the latter at same time as the solvent is removed.

As they are described, those polyesters become fluid at the melt temperature and have an excessive adhesiveness on any object to which they come in contact in the melt state. This adhesiveness in the melt state that leads to transfer of material does nevertheless disappear after hardening under cooling. Therefore the use of those polyesters in orthopedics has required various adaptations and one can observe that the condensation polyesters behave the same way.

In the U.S. Pat. No. 3,692,023, one uses a soft underlayer to keep the polymer out of sticking to the skin and hair that it covers when it is applied onto. In the same Patent, it is considered to preens the same polymer in sheets on a support or as a sandwich made of a knitted, woven or non-woven fabric with the assigned role is to prevent the flow of the material in the melt state. In the U.S. Pat. Nos. 4,273,115 and 4,316,457 pertaining to orthopedic bandages, one uses a polyethylene separator film which is wound together with the bandage to prevent its transformation in a mass at the time of its application. The U.S. Pat. No. 4,143,655 recommends another type of separator having multiple openings whereas the U.S. Pat. No. 4,454,873 allows to eliminate the bothering effect of a separator by the coating of an nonadherant and hydrosoluble polymer film on the material of the bandage itself. However, the latter solution has the drawbacks of progressive contamination of the water in the preparation hydrocollator and of significant reduction of the interlaminar strength between the various plies in a cylindrical cast in particular.

There are also physical adaptations which are inside the material containing those polyesters, It could be observed indeed that the type of Raschel knitted fabric with bulky strands made of shortcut fibers described in the U.S. Pat. No. 4,273,115 and 4,316,457 is absolutely necessary to suppress the effect of the to large fluidity of the polycaprolactones and of the linear polyurethanes related to, when applied in an orthopedic bandage for example. Those largely open strands have a very low apparent density and offer a volume between the fibers of about 80 per-cent. The U.S. Pat. No. 4,273,115 specifies moreover that the strands of fibers can only be partially impregnated with the polymer. The mechanical strength of those strands necessarily little tied up and partially impregnated is therefore rather weak and that can be seen in particular on the finished product impregnated with the resin and that can be easily torn by hand. The strand elements being so coated with polymer, the entirety is opposed to the fluid flow of the thermoadhesive constituent. However the latter remains highly deformable in a plastic manner, and the use of a roll of this material treated at the right temperature leads rapidly to a dense mass which becomes very hard to unwind if a separator polyethylene film has not been wound in the roll together with the bandage itself.

The new objectives presently aimed for in the applications based on this know-how are not satisfied by these aliphatic polyesters or these linear polyurethanes related to if they are applied separately.

Indeed, if one tries to apply the polymers described in the U.S. Pat. No. 4,273,115 and 4,316,457 onto a fabric or a knitted web having especially open mesh, and being of high tenacity which is possible only if strands are selected being more tightened, better tied up and made of continuous fibers, one must, in order to end up with the same surface weight of thermoadhesive resin, coat to a greater extent the outside part of the strands from which the resin which is no longer held by the fibers. It can then move in an undesirable manner and be transferred on the tools or the hands of the user during the application.

Moreover the knitted webs with bulky strands as recommended in those patents are soft to a point that they cannot be handled in a width under about one meter. Under those circumstances already, there is a narrowing of the warp strands caused by the traction and the weight when they are impregnated with the usual vertical processes also described in the same patents. Bandages of usual width are thus obtained in this case, by slitting the product after its impregnation in full width and drying. Such slitting operation results in sharp edges at the point where transverse threads have been cut. There is an obvious interest to obtain a bandage in useful width with uniform edges free of unevenness. However, with the textile construction that is required by the polymers described in the referenced patents, narrow width strips cannot hold themselves sufficiently and the final product comes out substantially narrower than at the beginning. Moreover, one observes concurrently with this type of bulky knitted web made of strands with short fibers, an elongation in the other direction which comes back at the time of heating for use preparation. Thus the textile substrates necessary for the polymers of the prior art do not allow a dimensionally stable product and it is necessary to prepare the strips by slitting after the polymer has been applied. If in other respects, one is interested with those impregnated knitted webs, not in view of a cylindrical cast but in view of laminated sheets for splints or orthoses, the user must take account for the shrinkage, sometimes up to 10 per-cent that arises during the preparatory heating of the sheet and this is inconvenient. There is therefore, an interest to use less deformable fabrics.

Knowing that tile applications of the products envisioned in the present invention comprise a cycle of heating and cooling, it is useful to define at least four characteristic temperatures of which it is also interesting to examine the values to appraise the advantages provided by the invention beyond the simple control of fluidity and adhesiveness.

The softening temperature (T1) is the temperature at which the material starts to lose its rigidity. In particular, it can be determined by the ASTM method No. 1043-87 or 1053-89 taking the inflection point of the curve of variation of modulus with temperature.

The treatment temperature (T2) for the application is the suited temperature at which it is required to bring the material In order that it has In an appropriate time, the desired formability and adhesive characteristics and retains them sufficiently during the time necessary to complete the application. It has to be noticed that during the application, the material cools by either a natural or forced way. Depending on the thickness of the material and the ambient temperature, that T2 temperature will be more or less high, necessarily above the the thermodynamic melting temperature of the semi-crystalline constituent in the combination.

The temperature (T3) is the temperature at which, during the cooling of the material, normally after completion of the application, the material starts losing its adhesive capability.

The temperature (T4) is the temperature at which, during the cooling of the material, normally after completion of the application, the material starts losing its capability to be shaped due to the increase of its rigidity.

In practice, one refers more often to the time (t3) after which the material is no longer adhesive and the time (t4) after which the material is no longer formable when it cools down in given thickness, in a given ambience and having applied a given treatment temperature. In such case, there is a parallel between t3 and T3 as well as between t4 and T4.

This distinction of the above four temperatures allows to specify the optimal characteristics of the envisioned products from that point of view.

In a general manner, the temperature T1 should be as high as possible above room temperature, temperature T2 should be as low as possible to allow easy application without risk of burns, which is particularly important in the instance of an orthopedic bandage. The temperature T3 should be as low as possible to provide the operator with a maximum delay t3 during the application. The optimal value of T4 depends on the application and on the time t4 the operator wants to have to complete his task. Time t4 must be sufficiently long but not to the point the operator has to wait for the evaluation of his work.

About those characteristic temperatures, let us notice that the German Patent DE-3605192 A1 suggests a mean to obtain precisely the shaping of a thermoadhesive sheet, which is not aimed to be laminated but rather to assemble shoe parts, at a temperature as low as possible under the temperature at which the sheet becomes adhesive, and this by a non totally covering coating only with a thermoadhesive product, of a substrate eventually impregnated by a polymer. It goes without saying that this know-how which targets in our nomenclature a maximum gap between T1 and T2, is not applicable in the domains envisioned by the present invention where one seeks, on the contrary, a dimensional stability of the composite in the largest temperature interval as possible.

The object of the present invention is to provide materials becoming easily moldable by hand up to large sizes of one square meter or two, after a treatment at the lowest possible temperature under 100° C., while retaining the properties at room temperature up to a temperature as high as possible above room temperature.

Another object of the present invention is to provide those materials in the form of thermoplastic orthopedic bandages, lightweight and aerated, exhibiting, without having to count on an inter-layer separator film, a good interlaminar strength, a good rigidity and a good resistance to tearing, such that the roll does not transform in a dense mass nor transfer the resin it contains on objects other than itself during Its hot application.

Another object of the present invention is to provide also those materials in the form of bandages soft or semi rigid that can be laminated after some temperature treatment and that become non sticky again when cold.

Another object of tile present invention is to provide those composites in the form of composite plaques or sheets easily moldable and adhesive to themselves, and which retain their shape as the molding progresses without risk of uncontrolled deformation due to exaggerated fluidity, so that a single operator can laminate a large size part such as a lombostat, a stage scenery or the negative print of an object on the average larger than a meter.

Another object of the present invention is to obtain those composites with inexpensive processes using as little as possible or no solvent.

Another object of the present invention is to make those materials recyclable and reusable.

In the present invention, one has obtained several means to control the fluidity at T2, the adhesiveness, the rigidity and the characteristic temperatures of thermoadhesive composites in the form of plaques, sheets or yet textiles with open mesh coated with such materials, formable and moldable under the conditions described above, of an easy working at a temperature that does not impede manual application in particular.

According to the present invention, it was found surprisingly that some composite combinations, of amorphous or semi-crystalline polymer structures that have a viscoelastic to rubbery behavior above a certain temperature, with a varying proportion depending on the application, of thermoplastic polymer structures, essentially semi-crystalline and comprising a minimum amount of aliphatic ester structural units, allow to overcome the difficulties cited above of a to large fluidity and of excessive adhesiveness, while providing new possibilities to modulate those characteristics as well as other useful characteristics in the application or use of resulting materials.

In the continuation of this description, one will name "first constituent" and "second constituent" respectively, the two above defined constituents of the combination as they are applied in sequence on a textile or plastic substrate.

The combination of the present invention comprises a first amorphous or semi-crystalline polymer constituent that is above its heat softening point at least at the temperature T2 and exhibiting at that same temperature at least a viscoelastic to rubbery behavior, and an essentially semi-crystalline second constituent with a content of aliphatic ester type structural units of at least about 80 per-cent and exhibiting at the temperature T2, an essentially plastic behavior, and such that the first constituent is applied in the first place on the substrate of the composite and the second constituent at the last place, forming a continuous film or covering completely the strands if, for example, the substrate is a knitted fabric with open mesh.

The combinations as described here before were found to be thermoadhesive in a fully satisfactory manner, without showing the inconvenience of uncontrolled deformation during the application. Through the selection of the proportion and the elements of the first constituents, and also to some extent by the selection of the elements of the second constituent, it has been observed that it was also possible to adjust the characteristic temperatures, the flexibility during the application and the rigidity of the finished product according to the needs.

According to the present invention, the second constituent is selected such that it has intrinsic thermoadhesive properties whereas the first constituent does not have them necessarily. Inversely, one has found that the first constituent has to provide the combination with a viscoelastic behavior when it is subjected to the temperature of the preparation treatment, which has been obtained with some first constituents having themselves a viscoelastic to rubbery behavior whereas the second constituent is only plastic at the same temperature.

In this manner, it was surprising to note that strips based on a knitted fabric with open mesh, impregnated firstly with a latex of a copolymer based on an acrylate, methacrylate, vinyl ester or of another polymer or copolymer having a heat softening temperature between $(-40)°$ C. and $(+60)°$ C., then dried, then covered with a polymer solution based on polycaprolactone or other means leading to a semi-crystalline thermoplastic polymer comprising at least 80 per cent of aliphatic ester type structural units, give, after evaporation of the solvent, a bandage that can easily be wound up and that, after immersing in a water bath set at 70° C., can be unwound without difficulty, whereas the same strip impregnated with the same equivalent total weight of the same polycaprolactone becomes an indivisible mass if an interlayer separator polyethylene film has not been put in place and this is surprising since the contact material at the interface is then identical in both cases.

In this embodiment of the invention, one has found that the rigidity of the dry bandage when it is finished, is directly related to the softening temperature of the first constituent, stiffer than a non composite bandage if the softening temperature of the first constituent Is above about 15° C. and less rigid in the opposite case.

In a first group of polymers used as the first constituent, the group of vinyl and acrylic or methacrylic ester polymers and copolymers appeared to be particularly interesting.

In this composite presentation of the material, the first constituent of vinyl, aczcylic, methacrylic or dienic type, is applied by impregnation or coating of a textile substrate in the first place, and It is then covered by the second constituent. Following this embodiment of the invention, a preferred embodiment is to apply this first constituent under the form of an aqueous dispersion such as a latex of the polymer or of the copolymer. One can this way apply a large quantity of solid matter without negative environmental impact. The second constituent covering the first one can be applied different ways, for example, by laying a polymer solution or a solution of monomers leading to the formation of the polymer on the substrate during or after the evaporation of the solvent.

This preferred embodiment of the invention gives access to a great variety of products such as thermoadhesive bandages which stay flexible and non sticky at room temperature if one chooses for the first constituent a latex of a polymer having a glass transition temperature under about 15° C. and in particular of about $(-20)°$ C., or large size immobilization devices which are relatively little deformable at temperatures between T2 and T4 so that they easily keep the shape that is given during the time t4 and which are of high rigidity at room temperature, if, on the contrary, one chooses for the first constituent, a latex of a polymer having a glass transition temperature in the interval T2 and T4, that is to say for example at about 40° C. as it can be obtained for example from emulsion polymerisation of isobutylmethacrylate or of a mixture of methylacrylate and ethylmethacrylate.

The combination possibilities are so many in this embodiment of the invention that it is not possible to tell them all. They allow in particular as already noted above, to obtain a product for which T3 is under T4 and this is unattainable with the prior art. One has been able to obtain such characteristics by applying a quantity above 50 per cent of a first constituent of the type of polyethylmethacrylate made in emulsion, then covering the latter with the second constituent based on polycaprolactone. After a treatment at 75° C., one sees the material is still adhesive while it has become almost rigid.

With this particular embodiment of the invention, one obtains in particular, bandages or composite products for splints, orthoses or other application, that can be either softer or stiffer than those provided by the prior art and having in the latter case, the capability to adjust the flexibility of the material for the time when it will be transformed, that is to say in the time interval t4.

In a second group of polymers used as the first constituent, it was found that It was possible to obtain the same effects with a copolymer such as, for example, of the polyurethane or polyurea type which has a viscoelastic to rubbery behavior at least at temperature T2 and in the interval T2 to T4, and eventually under T4 depending on the fact that the characteristics of this polyurethane govern the temperature T4 or that the latter is governed by the characteristics of the second constituent respectively.

One obtains the same type of effect as with the first constituents of vinyl or (meth)acrylate type.

One obtains fairly easily this constituent being viscelastic to rubbery at least a temperature T2, by reaction of a mixture of diol, triol and diisocyanate in particular, but one can obtain it also from bifunctional reagents only if in particular, one of them is intrinsically rubbery like polytetramethyleneglycol or a polypropyleneoxide. One can obviously use at the same time a triol and a rubbery diol.

This second type of first constituent of polyurethane nature, can moreover be amorphous or semi-crystalline at room temperature but in this latter case, its softening temperature must be under the envisioned T2 temperature, thus in any case under about 95° to 100° C. and preferably under 80° C. It goes without saying that the urethane reaction is not indispensable to form this type of first constituent in the combination and that any other chemical link can be suited.

In a preferred embodiment of the invention according this second family of first constituents, in particular if one seeks to obtain at room temperature a rigidity as high as possible, one chooses a polyurethane containing at least about 50 per-cent of crystallizable structural units and having a melting temperature under T2, such as based on an aliphatic ester having a molecular weight of at least about 2000 and preferably above 3000.

These combinations bear several decisive advantages in particular with respect to cyclic ester polymers alone as well as to linear urethane homopolymers of the prior art which as recalled above, require the type of substrate with bulky strands as well as a separator film for the winding of orthopedic bandage rolls.

It should also be noted that the present invention enlarges considerably the spectrum of resulting applications. It allows in particular to obtain a soft thermoadhesive bandage that proves to be useful for the treatment of a dislocation such as of the tendons.

In this application in a composite form representing the embodiment of the present invention, such as bandages or immobilization devices based on a textile substrate with open mesh in particular, it is also possible for the second group of first constituents, to dissociate the two constituents in a combination such that the first constituent of a viscoelastic to rubbery nature is laid or impregnated first and the second thermoadhesive constituent is laid next in a continuous film or as a complete envelope around the strands of a knitted fabric with open mesh. One obtains a similar effect and in a same way as when the first constituent is of polyvinyl or poly(meth)acrylate type.

For the two groups of first constituents, the ratio between the amount of the second constituent to the amount of the first one must be adjusted depending on the rubbery character of the first one, In a way that ensures a sufficient adhesive Joint, If the first constituent has characteristics of a relatively little deformable rubber, then an overall quantity of thermoadhesive second constituent greater than 50 per cent may be necessary for the possible contact area for lamination is relatively low. If the first constituent exhibits a sufficient: plasticity between T2 and T4, then an amount of second constituent less than 50 per cent may eventually be sufficient. From a simple geometric reasoning, indeed, one easily understands that a quantity of 49 per cent of first constituent for example leads, due to the concentric covering, to a thickness of the second constituent which is 30 per cent of the radius only, if the volume occupied by the textile is not taken into account. Therefore it is not surprising that this technique requires nevertheless a relatively large weight portion of thermoadhesive constituent, its effect being diminished by the geometry. As opposed to what could be expected however, one had to note that the stiffness properties of the resulting laminated composite are principally governed by the characteristics of the first constituent, and this is surprising If we think In terms of the strength of materials theory. Indeed, if reduced to a unit mass, a hollow pipe is always stiffer than a full rod.

It must hence be the composite effect after laminating that governs this rigidity. One has indeed obtained with this embodiment of the present invention, a composite material where the stiffness of each individual ply during the transformation (between T2 and T4) is lower than the one of an equivalent ply with a homogeneous composition, whereas the multiplies resulting composite is surprisingly found to have a greater stiffness.

In a general manner, the applications of the products of the present invention are much larger than those of the prior art. One can obtain materials indeed that are easily worked by hand, into circular casts, orthoses, external and supporting prostheses as well as soft thermoadhesive bandages which were not previously known. Furthermore, large size decorative structural elements are possible.

The thermoplastic orthopaedic bandages in particular can be directly fabricated in useful widths of 5, 10, and 15 centimeters for example and be finished with smooth and uniform edges. The thermoplastic splints and orthoses obtained by impregnation of a cloth can be, according to the present invention, dimensionally stable for the latter allows to use knitted fabrics with continuous fibers threads which are rather entangled, thereby preventing elongation during the impregnation process. In another respect, this embodiment of the present invention allows if one desires, to reinforce a more deformable fabric by first impregnation with a polymer as described and in particular, in the form of a latex for example.

The present invention allows one to vary the characteristic temperatures in a much larger range than with the prior art and obtain variable flexibility's and rigidities of the material not only during its application but also after it has set.

EXAMPLES

On a polyester cotton knitted fabric with 6 mm mesh size and weighing 151 g per square meter, one has applied successively by a dipping process, latex of acrylate-methacrylate copolymers with glass transition temperature of 11° C., 28° C. and 41° C. respectively. The dry strips were then covered by impregnation with a solution in methylenechloride comprising 483.8 g of polycaprolactone diol of molecular weight 4280, 3.4 g of polycaprolactone triol of equivalent weight of 184, 19.7 g of hexamethylenediisocyanate, about 300 g of solvent and 0.15 ml of dibutyltindilaurate. After oven treatment at 95° C., one obtains bandages with proportion of constituents given in the table 1, where is also given the glass transition temperature of the latex polymers and the apparent modulus after lamination of the bandage in three layers at 65° C.

TABLE 1

Weight ratios and flexural rigidity in relation with softening temperature of the first layer.

| | | | |
|---|---|---|---|
| Softening temperature | 11° C. | 28° C. | 41° C. |
| Fabric weight fraction | 0.17 | 0.17 | 0.17 |
| First layer weight fraction | 0.24 | 0.29 | 0.29 |
| Second layer weight fraction | 0.59 | 0.54 | 0.54 |
| Apparent flexural modulus (3 laminated plies) (MPa) | 156 | 242 | 380 |

The three types of strips wound in 2 meter long rolls and without a separator film, behave properly in the application on a limb when they have been treated In the water at 60° C. for one minute and form after about 5 minutes, a soft or rigid bandage depending on the softening temperature of the first constituent which is 11° C. in the first case and 41° C. in the latter.

I claim:

1. A composite composition of materials in flat or wound sheet offering uniformly distributed openings of size from 1 to 12 mm, leaving a free passage of at least 20 percent of the total surface, formable and adhesive to themselves at a temperature in a temperature interval from 35° C. to 90° C., and combining an open mesh textile substrate with specific weight not exceeding 500 g per square meter, whose body is successively impregnated or coated, then impregnated again and completely covered with at least two distinct materials, the first one, inside or on the surface of the substrate being of the group of polymers having a softening temperature not exceeding 80° C. and showing above that softening temperature a viscoelastic to rubbery but non fluid behavior, and the last one at the outer surface of the first ones, being of the group of semi crystalline polymers with a content of aliphatic ester type structural units of at least 80 percent and having a melting temperature comprised between 35° and 80° C. and having during a certain time after the fusion of an adhesive character on itself in a away the combination can be laminated in 2 or more layers.

2. A combination according to claim 1, wherein the substrate is an open net with mesh size from 1 to 12 mm.

3. A combination according to claim 1, wherein the substrate is an open knitted fabric with mesh size from 1 to 12 mm.

4. A combination according to claim 1, wherein the substrate is an open woven fabric where warp and weft threads leave openings from 1 to 12 mm.

5. A combination according to claim 1, wherein the substrate is a non woven fabric whose structure leaves openings from 1 to 12 mm.

6. A combination according to claim 1, wherein the substrate is a woven or non woven fabric perforated or expanded with openings from 1 to 12 mm.

7. A combination according to claim 6, wherein the first material is applied on the substrate before expansion or perforation.

8. A combination according to claim 6, wherein all the materials are applied on the substrate before expansion or perforation.

9. The combination according to claim 1 wherein the first material is in weight proportion of 10 to 90 per-cent and the second in weight proportion of 90 to 10 per-cent, the substrate weight being from 5 to 50 per-cent that of the whole combination.

10. The combination according to claim 1 wherein the first material is in weight proportion of 20 to 90 per-cent and the second in weight proportion of 80 to 10 per-cent, the substrate weight being from 5 to 50 per-cent that of the whole combination.

11. The combination according to claim 1 wherein the first material is in weight proportion of 10 to 80 per-cent and the second in weight proportion of 90 to 20 per-cent, the substrate weight being from 5 to 50 per-cent that of the whole combination.

12. The combination according to claim 1 wherein the first material is in weight proportion of 20 to 80 per-cent and the second in weight proportion of 80 to 20 per-cent, the substrate weight being from 5 to 50 per-cent that of the whole combination.

13. A combination according to claim 1 wherein the first material at least is a vinyl polymer or copolymer.

14. A combination according to claim 1 wherein the first material is a polymer or a copolymer of acrylic or methacrylic ester.

15. A combination according to claim 1 wherein the first material is a polymer or a copolymer of butadiene, chloroprene or isoprene.

16. A combination according to claim 1 wherein the first material is a copolymer of styrene or acrylonitrile with butadiene or chloroprene or isoprene.

17. A combination according to claim 1 wherein the first material is a copolymer of ethylene and acrylic, methacrylic or vinyl ester.

18. A combination according to claim 1 wherein the first material is a thermoplastic polyurethane.

19. A combination according to claim 1 wherein the first material is a polyurethane or a polyurea.

20. A combination according to claim 1 wherein the first material is a branched or partially or totally cross-linked polymer and comprises in proportion larger than 50 per-cent the structural unit of crystallizable aliphatic polyesters.

21. A thermoadhesive and thermomoldable structural material for successive lamination having a composition according to claim 2.

22. A three dimensional decorative element based on material according to claim 21.

23. A laminated part for single use framing in the molding of reinforced polyester resins, based on material according to claim 1.

24. A rigid bandage made by circular lamination after temperature treatment of a strip material according to claim 1.

25. A soft bandage made by circular lamination after temperature treatment of a strip material according to claim 1.

26. A supporting or immobilization device obtained by lamination at temperature of a sheet or plaque material according to claim 1.

27. A process allowing to obtain a composite combination of materials in flat or wound sheet offering uniformly distributed openings of size from 1 to 12 mm. leaving a free passage of at least 20 percent of the total surface, formable and adhesive to themselves at a temperature in the temperature interval from 35° C. to 90° C., and combining an open mesh textile substrate with specific weight not exceeding 500 g per square meter, whose body is successively impregnated or coated, then impregnated again and completely covered with at least two distinct materials, the first one, inside or on the surface of the substrate being of the group of polymers having a softening temperature not exceeding 80° C. and showing above that softening temperature a viscoelastic to rubbery but non fluid behavior, and the last one at the outer surface of the first ones, being of the group of semi crystalline polymers with a content of aliphatic ester type structural units of at least 80 per-cent and having a melting temperature comprised between 35° and 80° C. and having during a certain time after the fusion of an adhesive character on itself in a way the combination can be laminated in 2 or more layers,

- wherein the first material is a) a vinyl polymer or copolymer, b) a polymer or copolymer of acrylic or methacrylic ester, c) a polymer or copolymer of butadiene, chloroprene or isoprene, d) a copolymer of styrene or acrylonitrile with butadiene or chloroprene or isoprene, e) a copolymer of ethylene and acrylic, methacrylic or vinyl ester, f) a thermoplastic polyurethane, g) a polyurethane or polyurea or h) a branched or partially or totally cross-linked polymer having in proportion larger than 50 percent the structural unit of crystalizable aliphatic polyesters,
- wherein the first material is in whole or in part applied onto the substrate by layering or impregnation with or without a solvent, of a monomer or macromer reactive composition which is transformed in said material in the presence of the substrate, said eventual solvent is evaporated.

28. A process allowing to obtain a composite combination of materials in flat or wound sheet offering uniformly distributed openings of size from 1 to 12 mm. leaving a free passage of at least 20 percent of the total surface, formable and adhesive to themselves at a temperature in the temperature interval from 35° C. to 90° C., and combining an open mesh textile substrate with specific weight not exceeding 500 g per square meter, whose body is successively impregnated or coated, then impregnated again and completely covered with at least two distinct materials, the first one, inside or on the surface of the substrate being of the group of polymers having a softening temperature not exceeding 80° C. and showing above that softening temperature a viscoelastic to rubbery but non fluid behavior, and the last one at the outer surface of the first ones, being of the group of semi crystalline polymers with a content of aliphatic ester type structural units of at least 80 percent and having a melting temperature comprised between 35° and 80° C. and having during a certain time after the fusion of an adhesive character on itself in a away the combination can be laminated in 2 or more layers,

- wherein the first material is a) a vinyl polymer or copolymer, b) a polymer or copolymer of acrylic or methacrylic ester, c) a polymer or copolymer of butadiene, chloroprene or isoprene, d) a copolymer of styrene or acrylonitrile with butadiene or chloroprene or isoprene, e) a copolymer of ethylene and acrylic, methacrylic or vinyl ester, f) a thermoplastic polyurethane, g) a polyurethane or polyurea or h) a branched or partially or totally cross-linked polymer having in proportion larger than 50 percent the structural unit of crystalizable aliphatic polyesters,
- wherein the first material is in whole or in part applied onto the substrate by layering or impregnation of a polymer latex followed by the evaporation of the water it contains at a temperature that allows the coalescence of the polymer particles.

* * * * *